(12) United States Patent  
Dou et al.

(10) Patent No.: US 10,723,739 B2  
(45) Date of Patent: Jul. 28, 2020

(54) PROCESSES FOR THE PREPARATION OF RIBOCICLIB AND INTERMEDIATES THEREOF

(71) Applicant: Apotex Inc., Toronto (CA)

(72) Inventors: Daoke Dou, Tianjin (CN); Kangying Li, Tianjin (CN); Fuchang Zhang, Tianjin (CN); Jiang Pei, Tianjin (CN); Wancheng Guo, Tianjin (CN)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 16/410,137

(22) Filed: May 13, 2019

(65) Prior Publication Data

US 2019/0345163 A1    Nov. 14, 2019

Related U.S. Application Data

(60) Provisional application No. 62/671,025, filed on May 14, 2018.

(51) Int. Cl.
*C07D 487/04*    (2006.01)

(52) U.S. Cl.
CPC .................................. *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 8,324,225 B2 | 12/2012 | Brain et al. | |
| 8,415,355 B2 | 4/2013 | Brain et al. | |
| 9,193,732 B2 | 11/2015 | Calienni et al. | |
| 10,005,726 B2 | 6/2018 | Xu | |

FOREIGN PATENT DOCUMENTS

| | | |
|---|---|---|
| CN | 106478641 A | 3/2017 |
| CN | 106749259 A | 5/2017 |
| CN | 106928236 A | 7/2017 |
| CN | 106946880 A | 7/2017 |
| CN | 107118215 A | 9/2017 |
| CN | 107266451 A | 10/2017 |
| CN | 107936029 A | 4/2018 |
| CN | 108314686 A | 7/2018 |
| CN | 108586356 A | 9/2018 |
| CN | 108623599 A | 10/2018 |
| CN | 109553621 A | 4/2019 |
| WO | 2007140222 A2 | 12/2007 |
| WO | 2010020675 A1 | 2/2010 |
| WO | 2012064805 A1 | 5/2012 |
| WO | 2012115118 A1 | 8/2012 |
| WO | 2016192522 A1 | 12/2016 |
| WO | 2018051280 A | 3/2018 |
| WO | 2019082143 A1 | 5/2019 |

*Primary Examiner* — Susanna Moore  
(74) *Attorney, Agent, or Firm* — The Webb Law Firm

(57) ABSTRACT

The present invention provides processes for the preparation of Ribociclib, as well as intermediates useful in the preparation thereof. In particular, processes are provided for the preparation of a compound of Formula (4), and its conversion to Ribociclib (1).

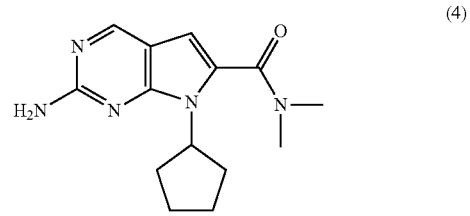

(4)

16 Claims, No Drawings

PROCESSES FOR THE PREPARATION OF RIBOCICLIB AND INTERMEDIATES THEREOF

CROSS-REFERENCE TO RELATED APPLICATION

This application claims the benefit of U.S. Provisional Patent Application No. 62/671,025, filed May 14, 2018, the disclosure of which is hereby incorporated in its entirety by reference.

TECHNICAL FIELD

The present invention relates to processes for the preparation of Ribociclib and intermediates used in the preparation thereof.

BACKGROUND

Ribociclib (1), or 7-cyclopentyl-N,N-dimethyl-2-{[5-(piperazin-1-yl) pyridin-2-yl]amino}-7H-pyrrolo[2,3-d]pyrimidine-6-carboxamide, in the form of a succinate salt, is the active ingredient in KISQALI®, which is indicated, in combination with an aromatase inhibitor, as initial endocrine-based therapy for the treatment of postmenopausal women with hormone receptor (HR)-positive, human epidermal growth factor receptor 2 (HER2)-negative, advanced or metastatic breast cancer.

(1)

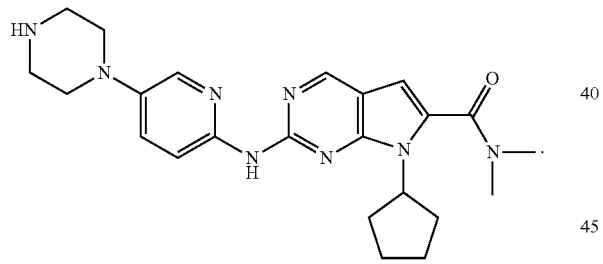

One method of preparing Ribociclib (1) is described in WO 2010/020675 A1, which discloses a family of compounds that are stated to be useful in treatments and therapies for protein kinase-associated disorders. In this method, which is depicted in Scheme 1, Ribociclib (1) is prepared by Buchwald-type coupling of pyrrolopyrimidine (H1) with the heteroaryl amine (I) to form the compound of formula (J), followed by deprotection of the tert-butoxycarbonyl (BOC)-protected piperazine ring. The pyrrolopyrimidine ring of intermediate (H1) is prepared by cyclization of intermediate (E1), formed from the respective displacement of the chloride and bromide substituents on the pyrrolidine ring of (A1) with cyclopentylamine (B) and masked propynal (C). Following hydrolysis of the acetal group of intermediate (E1), the resulting aldehyde (F1) is oxidized to the acid (G1), which then undergoes amidation with dimethylamine to provide the intermediate (H1).

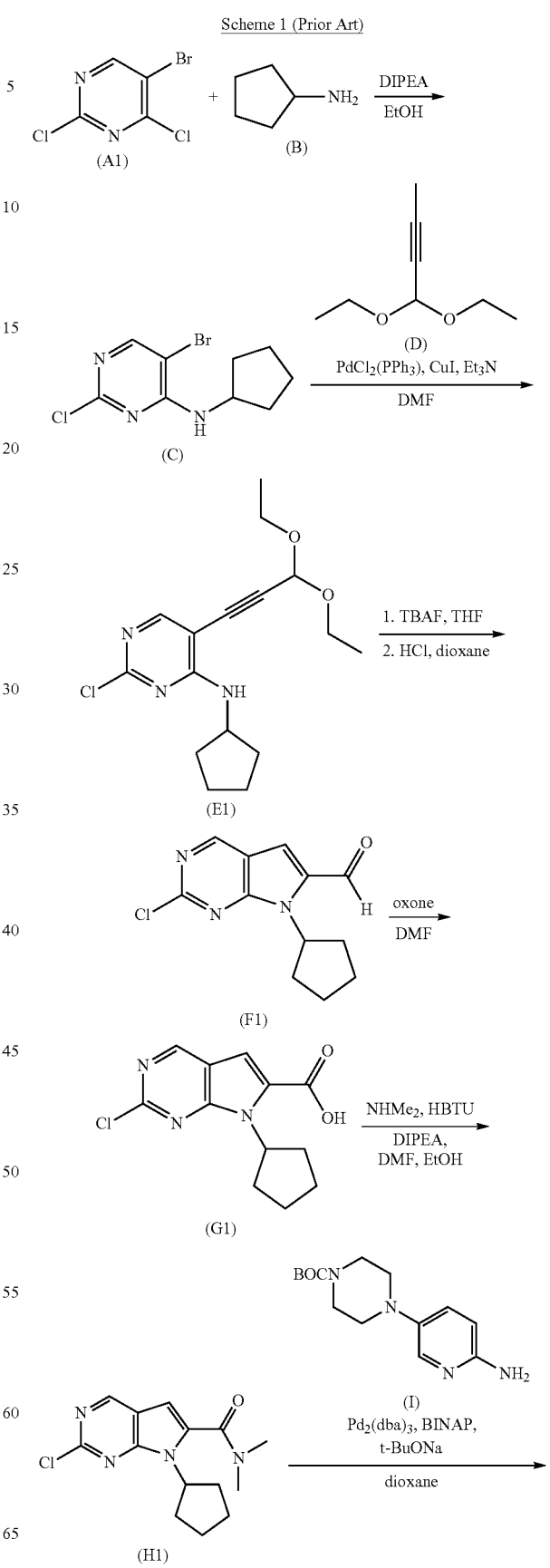

Scheme 1 (Prior Art)

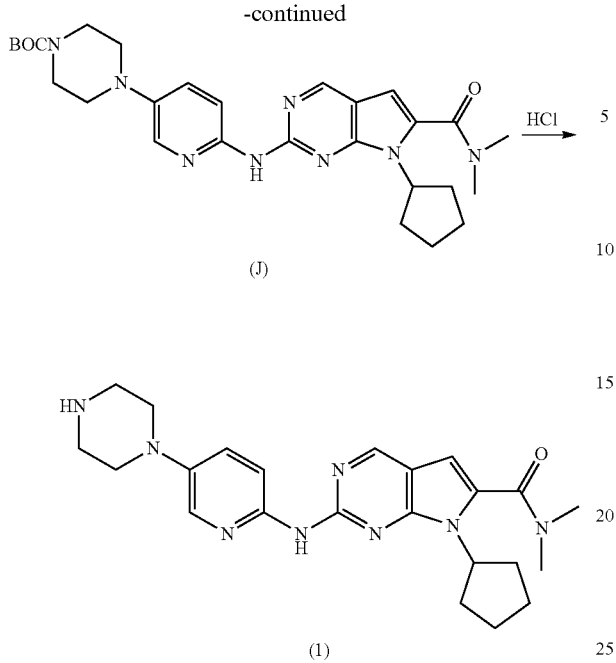

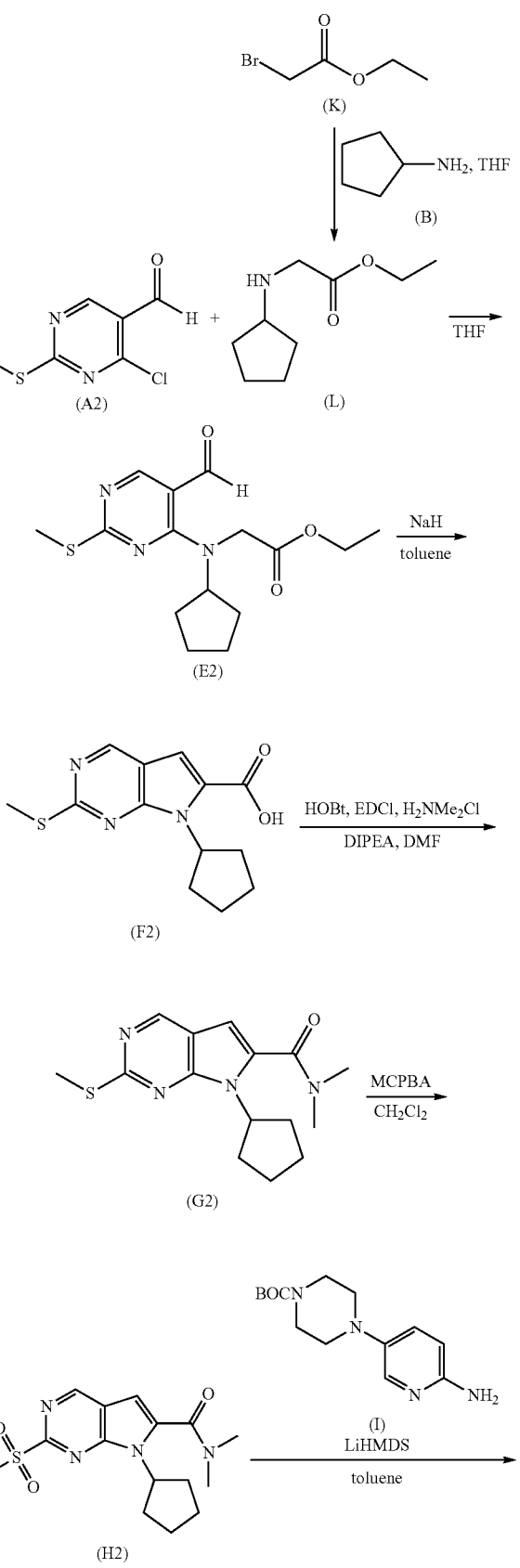

Scheme 2 (Prior Art)

A similar approach is reported in WO 2012/064805 A2, which uses propargyl alcohol rather than propargylaldehyde acetal (D) in formation of the pyrrolopyrimidine ring. Accordingly, subsequent steps to afford intermediate (H1) are altered and include an oxidation/amidation in the presence of manganese (IV) oxide, sodium cyanide and dimethylamine.

Although WO 2012/064805 A2 reports improved yields over WO 2010/020675 A1, and the elimination of chromatographic purification, these improvements necessitate the introduction of other disadvantages, such as the use of sodium cyanide, a highly toxic and hazardous substance requiring specialised transport, handling and disposal practices. Furthermore, the process requires a large excess of the oxidant, manganese (IV) oxide, which is a pigmented oxidant that stains surfaces and is notoriously difficult to remove from reactors and equipment. These factors lead to undue complexity and cost in the manufacture of Ribociclib (1) in a commercial setting.

A second strategy for the preparation of Ribociclib (1) is described in CN106749259 A. In this approach, which is exemplified in Scheme 2, Ribociclib (1) is prepared by displacement of the sulfonyl group of pyrrolopyrimidine (H2) with heteroaryl amine (I) to form the compound of formula (J), followed by deprotection of the tert-butoxycarbonyl (BOC)-protected piperazine ring. Unlike the prior approaches, the pyrrolopyrimidine ring of intermediate (H2) is prepared by an Aldol-type cyclization of intermediate (E2), which is formed from the displacement of the chloride substituent on the pyrrolidine ring of (A2) with cyclopentylamino ester (L). Following amidation of (F2) with dimethyl amine, the methyl sulfide is oxidized to the sulfone to afford intermediate (H2).

However, the use of chromatography for the purification of intermediate (J), and the use of excess amounts of hazardous and reactive reagents such as sodium hydride, meta-chloroperoxybenzoic acid (MCPBA), and lithium hexamethyldisilamide (LiHMDS), make this process impractical for use on a commercial scale.

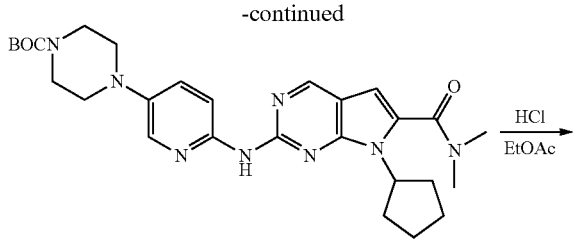

(J)

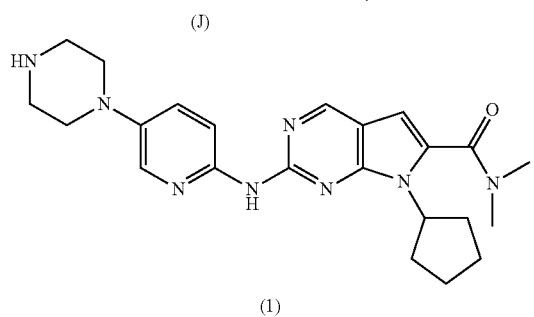

(1)

Owing to the drawbacks of the existing processes, there remains a need for improved processes for the preparation of Ribociclib (1), and the intermediates used in such preparations, that are more amenable to scale-up and use on a commercial scale.

SUMMARY OF THE INVENTION

The present invention provides improved processes for the preparation of Ribociclib (1), as well as new intermediates and processes for the preparation thereof, as depicted in Schemes 3, 4 and 5.

As shown in Scheme 3, in the processes of the present invention, Ribociclib (1) is prepared by coupling the compound of Formula (4) with the compound of Formula (3), followed by deprotecting the resulting intermediate of Formula (2). The key intermediate of Formula (4) may be prepared by amidating a compound of Formula (5-A) (i.e., the carboxylic acid of Formula (5-AA) or the ester of Formula (5-AB)). The acid of Formula (5-AA) may be prepared by either hydrolyzing the aliphatic ester of Formula (5-AB), or by hydrogenating the benzylic-type ester of Formula (6).

Scheme 3

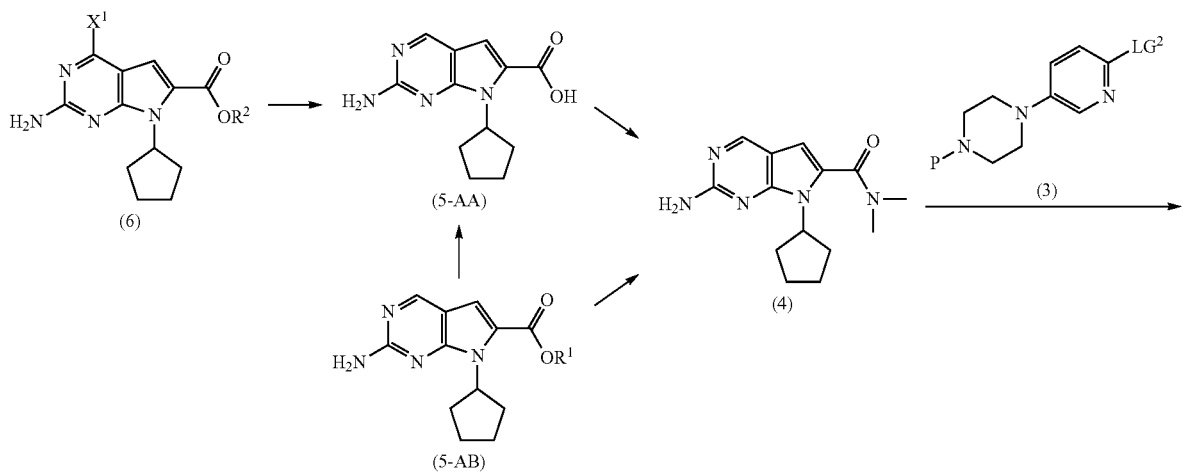

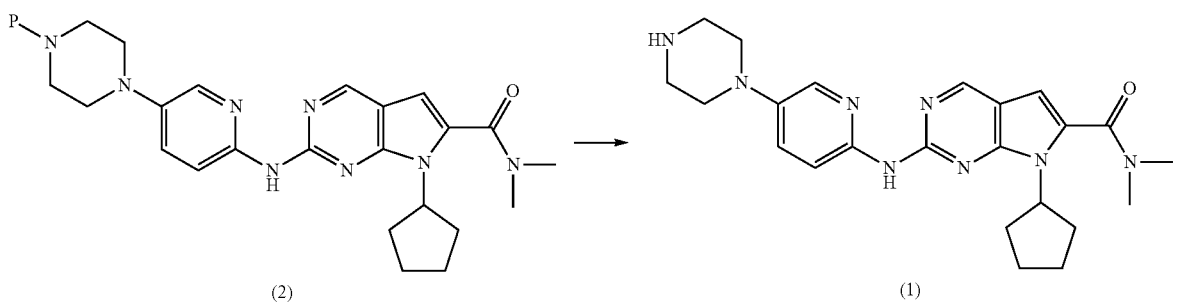

wherein

P is a protecting group;

R[1] is selected from the group consisting of a substituted or unsubstituted aliphatic group having 1 to 10 carbon atoms and a substituted or unsubstituted aryl group having 6 to 14 ring carbon atoms;

R[2] is $CR^aR^bR^c$;

$R^a$, $R^b$ and $R^c$ are three independent groups selected from the group consisting of H, a substituted aryl group having 6 to 14 ring carbon atoms, and an unsubstituted aryl group having 6 to 14 ring carbon atoms;

at least one of the groups $R^a$, $R^b$ and $R^c$ is a substituted aryl group having 6 to 14 ring carbon atoms or an unsubstituted aryl group having 6 to 14 ring carbon atoms;

X[1] is halide or H; and

LG[2] is a leaving group.

As shown in Scheme 4, in the processes of the present invention, the compound of Formula (6) may be prepared by reacting the cyclopentyl amine of Formula (11) with the acetate of Formula (10-A) to afford the compound of Formula (9-A). Following arylation with the pyrimidine of Formula (8), the resulting compound of Formula (7-A) undergoes cyclization to afford the compound of Formula (6).

Scheme 4

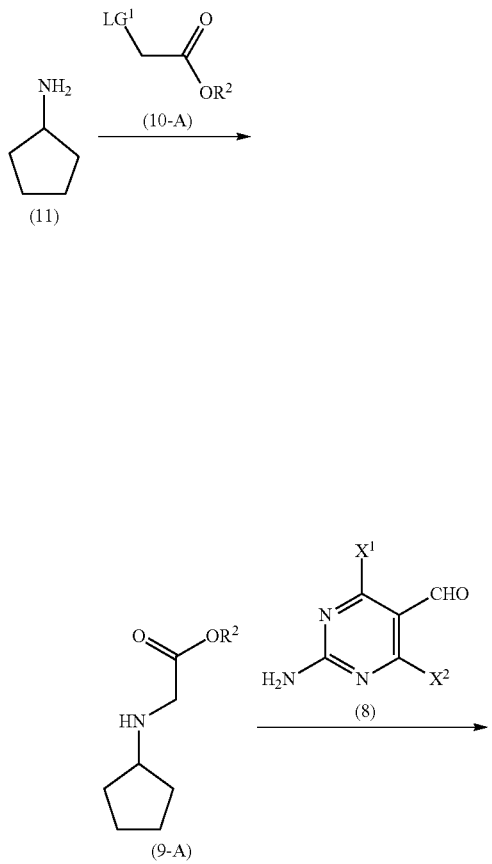

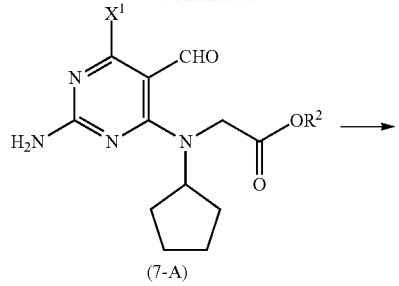

(7-A)

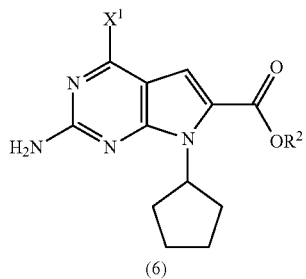

(6)

wherein

R[2] is $CR^aR^bR^c$;

$R^a$, $R^b$ and $R^c$ are three independent groups selected from the group consisting of H, a substituted aryl group having 6 to 14 ring carbon atoms, and an unsubstituted aryl group having 6 to 14 ring carbon atoms;

at least one of the groups $R^a$, $R^b$ and $R^c$ is a substituted aryl group having 6 to 14 ring carbon atoms or an unsubstituted aryl group having 6 to 14 ring carbon atoms;

X[1] is halide or H;

X[2] is halide; and

LG[1] is a leaving group.

As shown in Scheme 5, in the processes of the present invention, the compound of Formula (5-AB) may be prepared by reacting the cyclopentyl amine of Formula (11) with the acetate of Formula (10-B) to afford the compound of Formula (9-B). When X[1] is hydrogen, following arylation with the pyrimidine of Formula (8), the resulting compound of Formula (7-B) undergoes cyclization to provide the compound of Formula (5-AB). When X[1] is halide, following arylation with the pyrimidine of Formula (8), the resulting compound of Formula (7-B) is converted to the compound of Formula (5-AB) by hydrogenating the compound of Formula (7-B) followed by cyclizing the intermediate compound of Formula (7-BA), or by cyclizing the compound of Formula (7-B) followed by hydrogenating the intermediate compound of Formula (5-BB).

Scheme 5

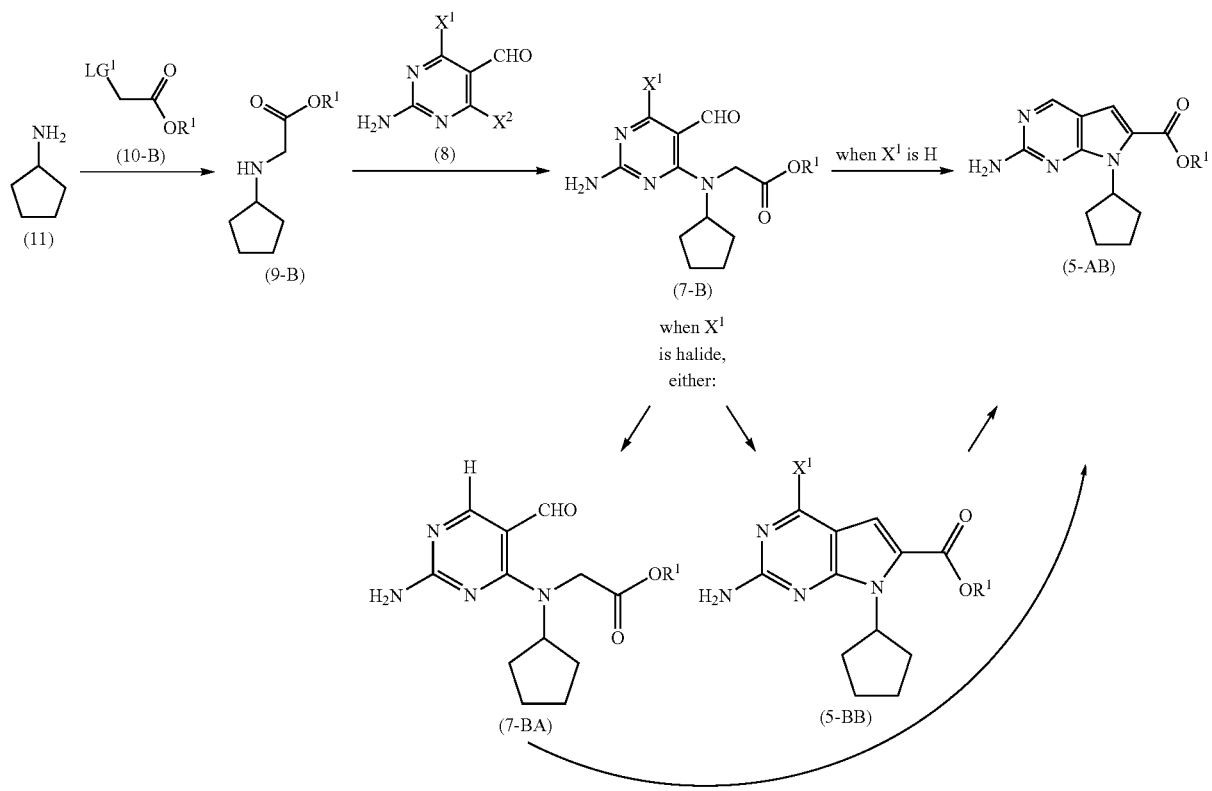

wherein
R[1] is selected from the group consisting of a substituted or unsubstituted aliphatic group having 1 to 10 carbon atoms, and a substituted or unsubstituted aryl group having 6 to 14 ring carbon atoms; and
X[1] is halide or H;
X[2] is halide; and
LG[1] is a leaving group.

The processes of the present invention are practical and industrially applicable, avoiding the use of hazardous or inconvenient reagents during the preparation of Ribociclib (1), which is provided in high overall yield, and the use of column chromatography during purification steps. In preferred embodiments, the processes of the present invention provide intermediate compounds having acceptable purity for downstream reactions following their isolation by simple filtration. Accordingly, the processes of the present invention provide important advantages that are applicable to the commercial preparation of Ribociclib (1).

Accordingly, in a first aspect of the present invention, there is provided a process for the preparation of Ribociclib (1), comprising:
(i) reacting, in the presence of a catalyst, a base (B7) and a solvent (S7), a compound of Formula (4) with a compound of Formula (3) to provide a compound of Formula (2), and
(ii) deprotecting the compound of Formula (2).

In a preferred embodiment of the first aspect, the catalyst is comprised of a palladium compound and a tertiary phosphine ligand. Preferably, the palladium compound is selected from the group consisting of palladium(II) chloride, palladium(II) bromide, palladium(II) acetate, palladium(II) acetylacetonate, bis(benzonitrile)palladium(II) chloride, palladium (II) trifluoroacetate, bis(acetonitrile)palladium(II) chloride, bis(triphenylphosphine)palladium(II) chloride, tris (dibenzylideneacetone)dipalladium (0), bis(dibenzylideneacetone)palladium (0) and tetrakis(triphenylphosphine) palladium (0). Preferably, the tertiary phosphine ligand is selected from the group consisting of 2,2'-bis(diphenylphosphino)-1,1'-binaphthalene, 4,5-bis(diphenylphosphino)-9,9-dimethylxanthene and 2-dicyclohexylphosphino-2',4',6'-triisopropylbiphenyl. Most preferably, the catalyst is comprised of bis(dibenzylideneacetone)palladium (0) and 4,5-bis(diphenylphosphino)-9,9-dimethylxanthene.

In another preferred embodiment of the first aspect, leaving group LG[2] in the compound of Formula (3) is selected from the group consisting of halide and a sulfonate. Preferably, leaving group LG[2] is chloride.

In another preferred embodiment of the first aspect, protecting group P in the compounds of Formulas (2) and (3) is selected from the group consisting of an alkyloxycarbonyl group, a carbobenzyloxycarbonyl group and a benzylic group. Preferably, protecting group P is a tert-butoxycarbonyl (BOC) group.

In further preferred embodiments of the first aspect, base (B7) is cesium carbonate, and solvent (S7) is 1,4-dioxane.

In another preferred embodiment of the first aspect, the compound of Formula (4) is prepared by the process of the second aspect of the invention as described below.

In a second aspect of the present invention, there is provided a process for the preparation of the compound of Formula (4) comprising amidating, in the presence of a solvent (S6), a compound of Formula (5-A) (a compound of Formula (5-AA) or (5-AB)) with dimethylamine, or a salt thereof.

In a preferred embodiment of the second aspect, the compound of Formula (5-A) is a compound of Formula (5-AA), and the step of amidating is conducted in the presence of an amide coupling agent selected from the group consisting of carbodiimides, uranium reagents and carbonyldiimidazoles. Preferably, the amide coupling agent is carbonyldiimidazole.

In another preferred embodiment of the second aspect, the compound of Formula (5-A) is a compound of Formula (5-AB). Preferably, in the compound of Formula (5-AB), the substituent $R^1$ is selected from the group consisting of C1-C6 alkyl. More preferably, the substituent $R^1$ is methyl.

In a further preferred embodiment of the second aspect, solvent (S6) is selected from the group consisting ethyl acetate, dichloromethane and N,N-dimethylformamide.

In another preferred embodiment of the second aspect, the compound of Formula (5-AA) is prepared by hydrolyzing a compound of Formula (5-AB). Preferably, the hydrolyzing step comprises treating the compound of Formula (5-AB) with a base (B5) in the presence of a solvent (S5), wherein the base (B5) is a metal hydroxide and the solvent (S5) is selected from the group consisting of ethanol, methanol, water and mixtures thereof.

In another preferred embodiment of the second aspect, the compound of Formula (5-AA) is prepared by a process comprising hydrogenating, in the presence of a solvent (S4) and a base (B4), a compound of Formula (6). Preferably, in the compound of Formula (6), $R^2$ is benzyl or substituted benzyl. In further preferred embodiments, the hydrogenating step comprises treating the compound of Formula (6) with hydrogen gas in the presence of a palladium on carbon catalyst; solvent (S4) is selected from the group consisting of ethers and esters; and base (B4) is a tertiary amine.

With this preferred embodiment, the compound of Formula (6) is preferably prepared by a process comprising:
(i) reacting, in the presence of a base (B1) and a solvent (S1), a compound of Formula (11) with a compound of Formula (10-A) to provide a compound of Formula (9-A);
(ii) reacting, in the presence of a base (B2) and a solvent (S2), the compound of Formula (9-A) with a compound of Formula (8) to provide a compound of Formula (7-A); and
(iii) cyclizing, in the presence of a base (B3) and a solvent (S3), the compound of Formula (7-A) to provide the compound of Formula (6)

Preferably, each of $X^1$, $X^2$ and $LG^1$ in the compounds of Formulas (7-A), (8), (9-1) and (10-A) is independently halide, and $R^2$ in the compounds of Formulas (7-A), (9-A) and (10-A) is benzyl or substituted benzyl. Also preferred is that each base (B1), (B2) and (B3) is independently a metal carbonate, and each solvent (S1), (S2) and (S3) is independently selected from the group consisting of ethers and esters.

In a further preferred embodiment of the second aspect, the compound of Formula (5-AB) is prepared by a process comprising:
(i) reacting, in the presence of a base (B1') and a solvent (S1'), a compound of Formula (11) with a compound of Formula (10-B) to provide a compound of Formula (9-B);
(ii) reacting, in the presence of a base (B2') and a solvent (S2'), the compound of Formula (9-B) with a compound of Formula (8) to provide a compound of Formula (7-B); and either:
(iiia) when $X^1$ in the compound of Formula (8) is hydrogen, cyclizing, in the presence of a base (B3') and a solvent (S3'), the compound of Formula (7-B) to provide the compound of Formula (5-AB); or
(iiib) when $X^1$ in the compound of Formula (8) is halide,
(a) hydrogenating, in the presence of a base (B4') and a solvent (S4'), the compound of Formula (7-B) to provide a compound of Formula (7-BA) (a compound of Formula (7-B) wherein $X^1$ is H), and cyclizing, in the presence of a base (B3') and a solvent (S3'), the compound of Formula (7-BA) to provide the compound of Formula (5-AB); or
(b) cyclizing, in the presence of a base (B3') and a solvent (S3'), the compound of Formula (7-B) to provide a compound of Formula (5-BB), and hydrogenating, in the presence of a base (B4') and a solvent (S4'), the compound of Formula (5-BB) to provide the compound of Formula (5-AB).

Preferably, in this embodiment of the second aspect, $R^1$ in the compounds of Formulas (5-BB), (7-BA), (7-B), (9-B) and (10-B) is C1-C6 alkyl, and each of $X^1$, $X^2$ and $LG^1$ in the compounds of Formulas (5-BB), (7-B) and (8) are independently halides. Most preferably, $R^1$ is methyl.

Further preferred within this embodiment is that the compound of Formula (5-AB) is prepared by the process comprising steps (i), (ii), (iii) and (iiib)(b).

Within this embodiment, when $R^1$ is C1-C6 alkyl, and $X^1$ is halide, the hydrogenating step comprises treating the compound of Formula (7-B) or the compound of Formula (5-BB) with hydrogen gas in the presence of a palladium on carbon catalyst.

Further preferred within this embodiment is that solvents (S1'), (S2'), (S3') and (S4') are each independently selected from the group consisting of ethers and esters; and that bases (B1), (B2) and (B3) are each independently a metal carbonate, and base (B1') is a tertiary amine.

In a third aspect of the invention, there is provided a compound of Formula (5) selected from the group consisting of a compound of Formula (5-A) and a compound of Formula (5-BB):

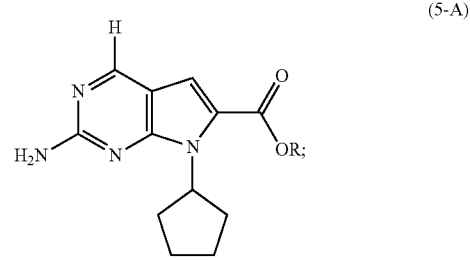

(5-A)

and

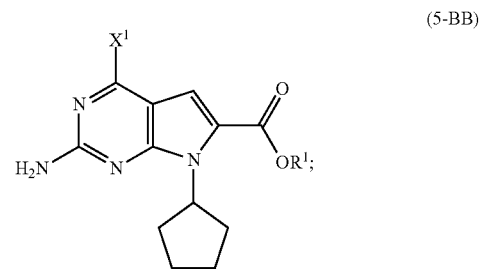

(5-BB)

wherein

R is selected from the group consisting of $R^1$ and H;

$R^1$ is selected from the group consisting of a substituted or unsubstituted aliphatic group having 1 to 10 carbon atoms and a substituted or unsubstituted aryl group having 6 to 14 ring carbon atoms; and $X^1$ is halide.

In a preferred embodiment of the third aspect, the compound of Formula (5) is a compound of Formula (5-A) and R is H.

In a fourth aspect of the invention, there is provided a compound of Formula (6):

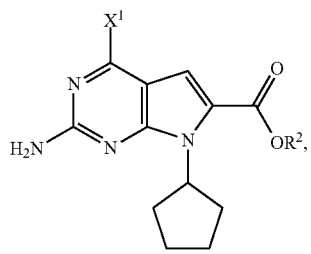

(6)

wherein $R^2$ is $CR^aR^bR^c$;

$R^a$, $R^b$ and $R^c$ are three independent groups selected from the group consisting of H, a substituted aryl group having 6 to 14 ring carbon atoms and an unsubstituted aryl group having 6 to 14 ring carbon atoms;

at least one of the groups $R^a$, $R^b$ and $R^c$ is a substituted aryl group having 6 to 14 ring carbon atoms or an unsubstituted aryl group having 6 to 14 ring carbon atoms; and $X^1$ is halide or H.

In a preferred embodiment of the fourth aspect, $R^2$ is benzyl and $X^1$ is chloride.

In a fifth aspect of the present invention, there is provided a compound selected from the group consisting of a compound of Formula (7-A):

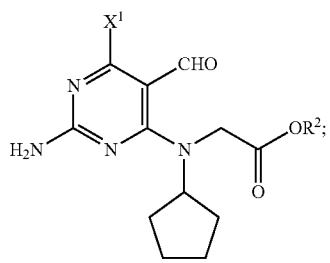

(7-A)

and a compound of Formula (7-B):

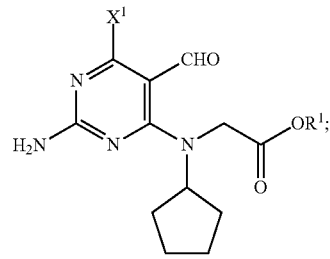

(7-B)

wherein $R^1$ is selected from the group consisting of a substituted or unsubstituted aliphatic group having 1 to 10 carbon atoms and a substituted or unsubstituted aryl group having 6 to 14 ring carbon atoms;

$R^2$ is $CR^aR^bR^c$;

$R^a$, $R^b$ and $R^c$ are three independent groups selected from the group consisting of H, a substituted aryl group having 6 to 14 ring carbon atoms and an unsubstituted aryl group having 6 to 14 ring carbon atoms;

at least one of the groups $R^a$, $R^b$ and $R^c$ is a substituted aryl group having 6 to 14 ring carbon atoms or an unsubstituted aryl group having 6 to 14 ring carbon atoms; and $X^1$ is halide or H.

In a preferred embodiment of the fifth aspect, the compound of Formula (7-A) is a compound wherein $R^2$ is benzyl and $X^1$ is chloride.

DETAILED DESCRIPTION

The processes of the present invention provide improvements in the preparation of Ribociclib (1) over known processes, including avoiding the use of hazardous reagents in the preparation of Ribociclib (1), and the use of column chromatography during purification steps, thereby providing processes that are more amenable to industrial application.

As used herein, the term "aliphatic", alone or as part of another substituent, means, unless otherwise stated, a straight chain, branched chain or non-aromatic cyclic hydrocarbon radical, or a combination thereof, which may be fully saturated, or mono- or polyunsaturated, and can include di- and multivalent radicals, having the number of carbon atoms designated. Examples of preferred saturated hydrocarbon radicals include methyl, ethyl, n-propyl, iso-propyl, n-butyl, t-butyl, iso-butyl, and sec-butyl. An unsaturated hydrocarbon radical is one having one or more double bonds or triple bonds. Examples of preferred unsaturated hydrocarbon radicals include vinyl, 2-propenyl, crotyl, 2-isopentenyl, 2-(butadienyl), 2,4-pentadienyl, 3-(1,4-pentadienyl), norbornenyl, ethynyl, 1-propynyl, 2-propynyl, and 3-butynyl. When there is no indication of the number of carbon atoms in the aliphatic group, it is meant, unless otherwise indicated by context, that there are from 1 to 10 carbons.

As used herein, the term "alkyl", alone or as part of another substituent, means, unless otherwise stated, a straight or branched chain, saturated hydrocarbon radical having the number of carbon atoms designated (e.g., C1-C4 means one to four carbon atoms). When there is no indication of the number of carbon atoms in the alkyl group, it is meant, unless otherwise indicated by context, that there are from 1 to 10 carbons. Examples of preferred saturated hydrocarbon groups include methyl, ethyl, n-propyl, isopropyl, n-butyl, t-butyl, iso-butyl and sec-butyl.

As used herein, the term "aryl", alone or as part of another substituent, means, unless otherwise stated, a polyunsaturated, aromatic, hydrocarbon radical which can be a single ring or multiple rings (preferably from 1 to 3 rings), which are fused together or linked covalently, having the number of ring carbon atoms designated. When there is no indication of the number of carbon atoms in the aryl group, it is meant, unless otherwise indicated by context, that there are from 6 to 14 ring carbons. Preferred examples of aryl groups include phenyl, 1-naphthyl, 2-naphthyl, 2-anthryl and 9-anthryl.

As used herein, the term "substituted" refers to the replacement of one or more hydrogen atoms with a non-hydrogen atom or multiple atoms of which at least one is a non-hydrogen atom. A substituted group (e.g., substituted —CH$_2$CH$_3$) may be fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). Substituted compounds or groups may comprise substituents selected from the group consisting of: alkyl, OR", halogen, CN, NO$_2$ and CF$_3$. As used herein, each R" may be selected, independently, from the group consisting of hydrogen and alkyl groups. Preferred examples of substituent groups on substituted aliphatic and aryl groups include methoxy, methyl, nitro, fluoride and chloride.

As used herein, the terms "wt %" refers to weight percent, and is used to express weight part/weight total as a percentage.

As used herein, "room temperature" generally refers to a temperature of 20-25° C.

As used herein, the term "about" means "close to", and that variation from the exact value that follows the term is within amounts that a person of skill in the art would understand to be reasonable. For example, when the term "about" is used with respect to temperature, a variation of ±5° C. is generally acceptable when carrying out the processes of the present invention, and when used with respect to mole equivalents, a variation of ±0.1 moles is generally acceptable.

In one embodiment of the present invention, Ribociclib (1) and intermediates useful in the preparation thereof may be prepared by the processes as set out in Schemes 3, 4 and 5. Exemplary reagents and conditions for these processes are described herein.

In the processes and compounds of the invention, $R^1$ is selected from the group consisting of a substituted or unsubstituted aliphatic group having 1 to 10 carbon atoms and a substituted or unsubstituted aryl group having 6 to 14 ring carbon atoms.

Preferably, when $R^1$ is an aliphatic group, the aliphatic group is selected from the group consisting of methyl, ethyl, n-propyl, isopropyl, n-butyl, t-butyl, isobutyl, and sec-butyl. More preferably, the aliphatic group is C1-C2 alkyl, and most preferably, the aliphatic group is methyl. Substituted aliphatic groups are preferably substituted with methoxy.

Preferably, when $R^1$ is an aryl group, the aryl group is selected from the group consisting of phenyl, 1-naphthyl, 2-naphthyl and 4-biphenyl, and is most preferably phenyl. Substituted aryl groups are preferably substituted with one or more substituents selected from the group consisting of halogen and nitro, and most preferably chloride, fluoride and nitro.

Most preferably, $R^1$ is methyl.

In the processes and compounds of the invention, $R^2$ is $CR^aR^bR^c$, $R^a$, $R^b$ and $R^c$ are three independent groups selected from the group consisting of H, a substituted aryl group having 6 to 14 ring carbon atoms, and an unsubstituted aryl group having 6 to 14 ring carbon atoms, wherein at least one of the groups $R^a$, $R^b$ and $R^c$ is a substituted or unsubstituted aryl group having 6 to 14 ring carbon atoms. Preferably, one of $R^a$, $R^b$ and $R^c$ is a substituted or unsubstituted aryl group having 6 to 14 carbon atoms and the remaining groups are each H.

Preferably, when $R^a$, $R^b$ or $R^c$ is an aryl group, the aryl group is selected from the group consisting of phenyl, 1-naphthyl, 2-naphthyl, 2-anthryl and 9-anthryl, most preferably phenyl. Substituted aryl groups are preferably substituted with one or more substituents selected from the group consisting of methyl, methoxy and halogen, most preferably, methyl and methoxy.

Most preferably, $R^2$ is benzyl.

In the processes and compounds of the invention, $X^1$ is halide or H, and $X^2$ is halide. Halide is preferably selected from the group consisting of chloride, bromide and iodide, and is most preferably chloride. Preferably, both $X^1$ and $X^2$ are chloride.

P is a protecting group, preferably selected from the group consisting of alkyloxycarbonyl groups, benzyloxycarbonyl groups and benzylic groups. Preferred protecting groups are selected from the group consisting of tert-butoxycarbonyl (BOC), benzyloxycarbonyl (CBz), benzyl (Bn) and methoxy substituted benzyl (for example, PMB). Most preferably, P is tert-butoxycarbonyl.

$LG^1$ is a leaving group, preferably selected from the group consisting of halides and sulfonates. Preferred sulfonates are selected from methane sulfonate, toluene sulfonate and trifluoromethane sulfonate. Preferred halides are selected from the group consisting of chloride, bromide and iodide. Preferably, $LG^1$ is halide, and most preferably, bromide.

$LG^2$ is a leaving group, preferably selected from the group consisting of halides and sulfonates. Preferred halides are selected from the group consisting of chloride, bromide and iodide. Preferred sulfonates are selected from methane sulfonate, toluene sulfonate and trifluoromethane sulfonate. Preferably, $LG^2$ is halide, and is most preferably chloride.

In another embodiment of the present invention, there is provided a process for the preparation of the compound of Formula (9-A):

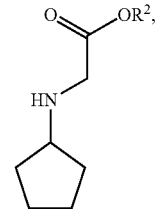

(9-A)

comprising, reacting, in the presence of a base (B1) and a solvent (S1), a compound of Formula (11):

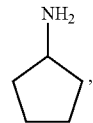

(11)

with a compound of Formula (10-A):

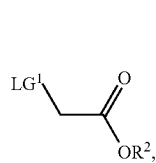

(10-A)

wherein
  $R^2$ is $CR^aR^bR^c$;
  $R^a$, $R^b$ and $R^c$ are three independent groups selected from the group consisting of H, a substituted aryl group having 6 to 14 ring carbon atoms and an unsubstituted aryl group having 6 to 14 ring carbon atoms;
  at least one of the groups $R^a$, $R^b$ and $R^c$ is a substituted aryl group having 6 to 14 ring carbon atoms or an unsubstituted aryl group having 6 to 14 ring carbon atoms; and
  $LG^1$ is a leaving group.

The reaction of the compound of Formula (11) and the compound of Formula (10-A) is conducted in the presence of a solvent (S1). Solvent (S1) is preferably selected from the group consisting of ethers, esters, ketones, hydrocarbons, amides, sulfoxides, alcohols, water and mixtures thereof. More preferably, solvent (S1) is selected from the group consisting of methyl t-butyl ether, tetrahydrofuran, ethyl acetate, acetone, toluene, N,N-dimethylformamide, dimethyl sulfoxide, ethanol, water and mixtures thereof. Most preferably, solvent (S1) is ethyl acetate.

The reaction of the compound of Formula (11) and the compound of Formula (10-A) is conducted in the presence of a base (B1). Base (B1) may be any suitable inorganic or amine base, including the compound of Formula (11). Base (B1) is preferably selected from the group consisting of tertiary amines, metal carbonates and metal bicarbonates. More preferably, base (B1) is selected from the group consisting of sodium carbonate, sodium bicarbonate, potassium carbonate, potassium bicarbonate, lithium carbonate, triethylamine and N,N-diisopropylethylamine. Most preferably, base (B1) is potassium carbonate.

The reaction of the compound of Formula (11) and the compound of Formula (10-A) may be conducted at any suitable temperature, and is preferably conducted at a temperature between about 0° C. and about 50° C., more preferably between about 20° C. and about 30° C.

The compound of Formula (11) is a commercially available compound. In some cases, the compound of Formula (10-A) is a commercially available compound. Alternatively, the compound of Formula (10-A) may be prepared by any desired method including, for example, esterification of the appropriate haloacetyl halide or sulfonylation of the appropriate glycolic acid ester.

In another embodiment of the present invention, there is provided a process for the preparation of the compound of Formula (7-A):

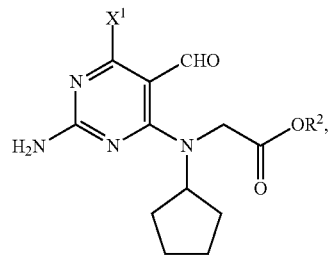

(7-A)

comprising reacting, in the presence of a base (B2) and a solvent (S2), the compound of Formula (9-A):

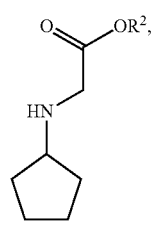

(9-A)

with a compound of Formula (8):

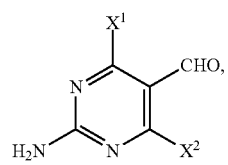

(8)

wherein
  $R^2$ is $CR^aR^bR^c$;
  $R^a$, $R^b$ and $R^c$ are three independent groups selected from the group consisting of H, a substituted aryl group having 6 to 14 ring carbon atoms and an unsubstituted aryl group having 6 to 14 ring carbon atoms;
  at least one of the groups $R^a$, $R^b$ and $R^c$ is a substituted aryl group having 6 to 14 ring carbon atoms or an unsubstituted aryl group having 6 to 14 ring carbon atoms;
  $X^1$ is halide or H; and
  $X^2$ is halide.

The reaction of the compound of Formula (9-A) and the compound of Formula (8) is conducted in the presence of a solvent (S2). Solvent (S2) is preferably selected from the group consisting of ethers, esters, alcohols and nitriles. More preferably, solvent (S1) is selected from the group consisting of methyl t-butyl ether, tetrahydrofuran, ethyl acetate, ethanol and acetonitrile. Most preferably, solvent (S1) is ethyl acetate.

The reaction of the compound of Formula (9-A) and the compound of Formula (8) is conducted in the presence of a base (B2). Base (B2) may be any suitable inorganic or tertiary amine base. Preferably, base (B2) is selected from the group consisting of tertiary amines, metal carbonates and metal bicarbonates. More preferably, base (B2) is selected from the group consisting of sodium carbonate, sodium bicarbonate, potassium carbonate, potassium bicarbonate, lithium carbonate, triethylamine and N,N-diisopropylethylamine. Most preferably, base (B2) is potassium carbonate or triethylamine.

The reaction of the compound of Formula (9-A) and the compound of Formula (8) may be conducted at any suitable temperature, and is preferably conducted at a temperature between about 0° C. and about 80° C., more preferably between about 20° C. and about 30° C.

Many of the compounds of Formula (9-A) are commercially available compounds. Alternatively, or to the extent a compound of Formula (9-A) is not commercially available, the compounds of Formula (9-A) can be prepared using standard methods from the corresponding carboxylic acid.

In another embodiment of the present invention, there is provided a process for the preparation of the compound of Formula (6):

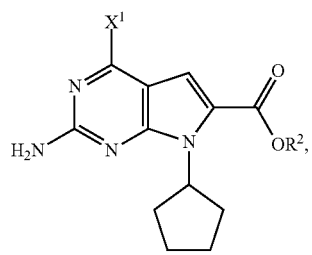

(6)

the process comprising, cyclizing, in the presence of a base (B3) and a solvent (S3), of the compound of Formula (7-A):

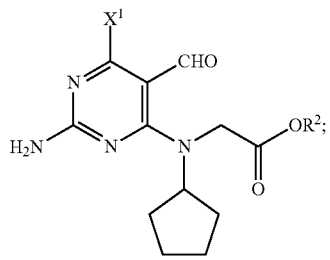

(7-A)

wherein
  $R^2$ is $CR^aR^bR^c$;
  $R^a$, $R^b$ and $R^c$ are three independent groups selected from the group consisting of H, a substituted aryl group having 6 to 14 ring carbon atoms and an unsubstituted aryl group having 6 to 14 ring carbon atoms;
  at least one of the groups $R^a$, $R^b$ and $R^c$ is a substituted aryl group having 6 to 14 ring carbon atoms or an unsubstituted aryl group having 6 to 14 ring carbon atoms; and
  $X^1$ is halide or H.

The cyclization of the compound of Formula (7-A) is conducted in the presence of a solvent (S3). Solvent (S3) is preferably selected from the group consisting of ethers, esters, alcohols, amides, aromatic hydrocarbons and nitriles. More preferably, solvent (S3) is selected from the group consisting of methyl t-butyl ether, tetrahydrofuran, ethyl acetate, ethanol N,N-dimethylformamide, toluene and acetonitrile. Most preferably, solvent (S3) is ethyl acetate.

The cyclization of the compound of Formula (7-A) is conducted in the presence of a base (B3). Base (B3) may be any base of suitable strength. Preferably, base (B3) is selected from the group consisting of metal hydroxides, metal hydrides and metal carbonates. More preferably, base (B3) is selected from the group consisting of sodium hydroxide, sodium hydride and cesium carbonate. Most preferably, base (B3) is cesium carbonate.

The cyclization of the compound of Formula (7-A) may be conducted at any suitable temperature. Depending on the choice of reaction conditions, such as base (B3), the reaction may be conducted at a temperature between about 0° C. and about 100° C. Lower temperatures are preferable when the base (B3) is a stronger base, such as sodium hydride, whereas higher temperatures are preferable when the base (B3) is a weaker base, such as cesium carbonate. Preferably, the temperature is between about 0° C. and 50° C.

In another embodiment of the present invention, there is provided a process for the preparation of the compound of Formula (5-AA):

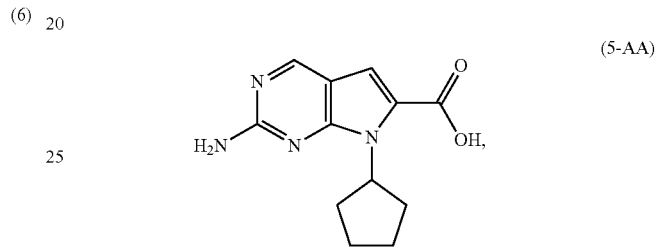

(5-AA)

comprising, hydrogenating, in the presence of a solvent (S4) and a base (B4), a compound of Formula (6):

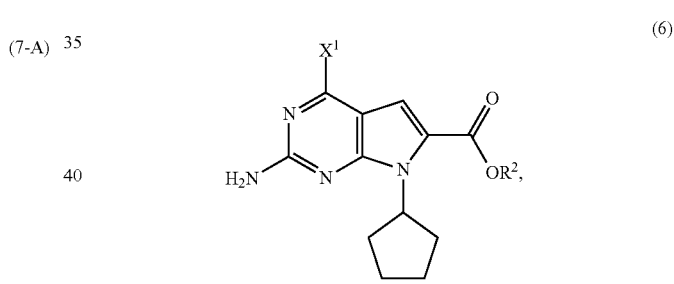

(6)

wherein
  $X^1$ is halide or H;
  $R^2$ is $CR^aR^bR^c$;
  $R^a$, $R^b$ and $R^c$ are three independent groups selected from the group consisting of H, a substituted aryl group having 6 to 14 ring carbon atoms and an unsubstituted aryl group having 6 to 14 ring carbon atoms; and
  at least one of the groups $R^a$, $R^b$ and $R^c$ is a substituted aryl group having 6 to 14 ring carbon atoms or an unsubstituted aryl group having 6 to 14 ring carbon atoms.

The hydrogenation of the compound of Formula (6) is preferably conducted with hydrogen gas in the presence of a suitable transition metal catalyst. Preferably, the suitable transition metal catalyst is selected from the group consisting of palladium, platinum and Raney-nickel hydrogenation catalysts. The suitable catalyst may be finely dispersed solids or, preferably, is adsorbed on an inert support, such as carbon or alumina, and may be wet or dry. Preferably, the suitable catalyst is palladium on carbon (Pd/C). More preferably, the catalyst is 5 wt % palladium on carbon. The catalyst loading may be from about 0.1 wt % to about 1 wt % palladium with respect to the weight of the compound of Formula (6). Preferably, the catalyst loading is about 0.2 wt % palladium with respect to the weight of the compound of Formula (6).

The hydrogenation of the compound of Formula (6) is conducted in the presence of a solvent (S4). Solvent (S4) is preferably selected from the group consisting of ethers, esters and alcohols. More preferably, solvent (S4) is selected from the group consisting of tetrahydrofuran, ethyl acetate and ethanol. Most preferably, solvent (S4) is ethanol.

The hydrogenation of the compound of Formula (6) is conducted in the presence of a base (B4). Base (B4) may be any suitable inorganic or tertiary amine base. Base (B4) is preferably selected from the group consisting of tertiary amines, metal carbonates and metal bicarbonates. Preferably, base (B4) is selected from the group consisting of sodium carbonate, sodium bicarbonate, potassium carbonate, potassium bicarbonate, lithium carbonate, triethylamine and N,N-diisopropylethylamine. Most preferably, base (B4) is triethylamine.

The hydrogenation of the compound of Formula (6) may be conducted at any suitable temperature and is preferably conducted at a temperature between about 0° C. and about 50° C., more preferably between about 20° C. and about 30° C.

In another embodiment of the present invention, there is provided a process for the preparation of the compound of Formula (9-B):

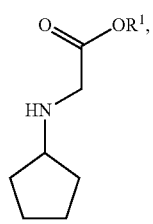

(9-B)

comprising reacting, in the presence of a base (B1') and a solvent (S1'), a compound of Formula (11):

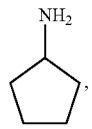

(11)

with a compound of Formula (10-B):

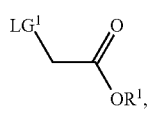

(10-B)

wherein
R$^1$ is selected from the group consisting of a substituted or unsubstituted aliphatic group having 1 to 10 carbon atoms, and a substituted or unsubstituted aryl group having 6 to 14 ring carbon atoms; and
LG$^1$ is a leaving group.

The process for the preparation of the compound of Formula (9-B) may be conducted in accordance with the process described herein for the preparation of the analogous compound of Formula (9-A). Thus, suitable LG$^1$, base (B1'), solvent (S1'), and temperature of the reaction are in accordance with LG$^1$, base (B1), solvent (S1), and temperature of the corresponding process for the preparation of the compound of Formula (9-A). Additionally, procedures for the preparation of compounds of Formula (10-A) are applicable to the preparation of compounds of Formula (10-B).

In another embodiment of the present invention, there is provided a process for the preparation of the compound of Formula (7-B):

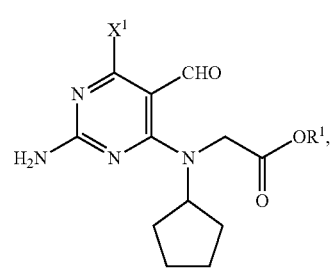

(7-B)

comprising reacting, in the presence of a base (B2') and a solvent (S2'), the compound of Formula (9-B):

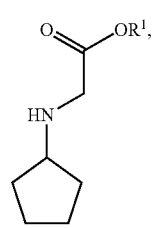

(9-B)

with a compound of Formula (8):

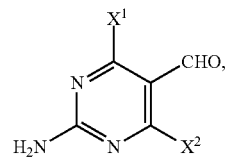

(8)

wherein
R$^1$ is selected from the group consisting of a substituted or unsubstituted aliphatic group having 1 to 10 carbon atoms and a substituted or unsubstituted aryl group having 6 to 14 ring carbon atoms;
X$^1$ is halide or H; and
X$^2$ is halide.

The process for the preparation of the compound of Formula (7-B) may be conducted in accordance with the process described herein for the preparation of the analogous compound of Formula (7-A). Thus, suitable X$^1$, X$^2$, base (B2'), solvent (S2'), and temperature of the reaction are in accordance with X$^1$, X$^2$, base (B2), solvent (S2), and temperature of the corresponding process for the preparation of the compound of Formula (7-A).

In another embodiment of the present invention, there is provided a process for the preparation of the compound of Formula (5-AB):

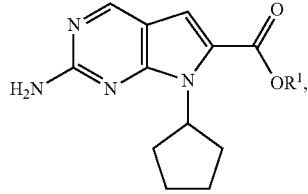
(5-AB)

comprising cyclizing, in the presence of a base (B3') and a solvent (S3'), of the compound of Formula (7-BA):

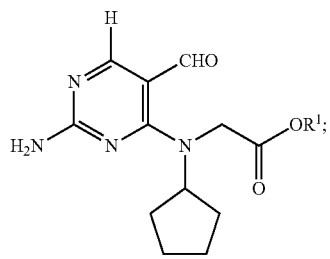
(7-BA)

wherein
X¹ is H; and
R¹ is selected from the group consisting of a substituted or unsubstituted aliphatic group having 1 to 10 carbon atoms and a substituted or unsubstituted aryl group having 6 to 14 ring carbon atoms.

The cyclization of the compound of Formula (7-B) may be conducted in accordance with the cyclization of the analogous compound of Formula (7-A) described herein. Thus, suitable base (B3'), solvent (S3'), and temperature of the reaction are in accordance with base (B3), solvent (S3) and temperature of the corresponding process for cyclizing the compound of Formula (7-A).

In another embodiment of the present invention, there is provided a process for the preparation of the compound of Formula (5-AB):

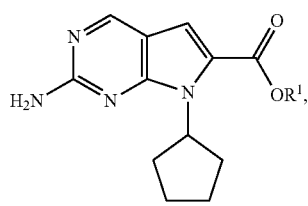
(5-AB)

comprising:
hydrogenating, in the presence of a base (B4') and a solvent (S4'), the compound of Formula (7-B):

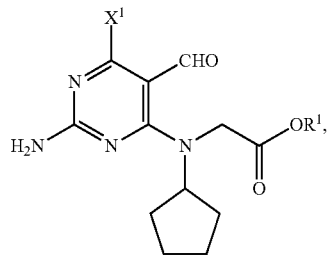
(7-B)

to provide a compound of Formula (7-BA):

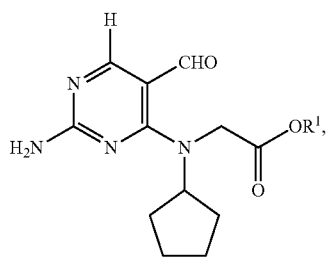
(7-BA)

and
cyclizing, in the presence of a base (B3') and a solvent (S3'), of the compound of Formula (7-BA) to provide the compound of Formula (5-AB),
wherein
X¹ is halide; and
R¹ is selected from the group consisting of a substituted or unsubstituted aliphatic group having 1 to 10 carbon atoms and a substituted or unsubstituted aryl group having 6 to 14 ring carbon atoms.

Hydrogenation of the compound of Formula (7-B) may be conducted in accordance with the process described herein for hydrogenating the compound of Formula (6). Thus, suitable hydrogenation conditions (including the hydrogen source and catalyst), base (B3'), solvent (S3'), and temperature of the reaction are in accordance with the hydrogenating conditions, base (B4), solvent (S4) and temperature of the corresponding process for hydrogenating the compound of Formula (6).

The cyclization of the compound of Formula (7-BA) may be conducted in accordance with the process described herein for the cyclization of the compound of Formula (7-B). Thus, using suitable base (B3'), solvent (S3'), and corresponding temperature of the reaction in accordance with the process for cyclizing the compound of Formula (7-B).

In another embodiment of the present invention, there is provided an alternative process for the preparation of the compound of Formula (5-AB):

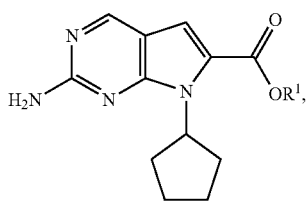
(5-AB)

comprising:

cyclizing, in the presence of a base (B3') and a solvent (S3'), the compound of Formula (7-B):

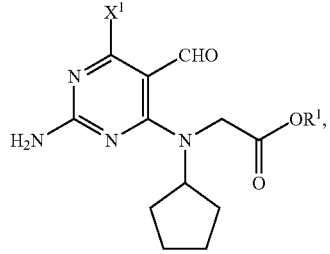

(7-B)

to provide the compound of Formula (5-BB):

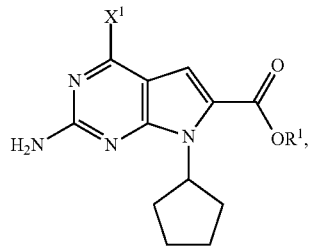

(5-BB)

and hydrogenating, in the presence of a base (B4') and a solvent (S4'), the compound of Formula (5-BB) to provide the compound of Formula (5-AB), wherein X$^1$ is halide; and R$^1$ is selected from the group consisting of a substituted or unsubstituted aliphatic group having 1 to 10 carbon atoms and a substituted or unsubstituted aryl group having 6 to 14 ring carbon atoms.

The process for the preparation of the compound of Formula (5-AB), comprising cyclizing the compound of Formula (7-B) followed by hydrogenating the compound of Formula (5-BB), may be conducted in accordance with the process described herein for the preparation of the compound of Formula (5-AB) comprising the steps of hydrogenating the compound of Formula (7-B) followed by cyclizing the resulting compound of Formula (7-BA) (i.e., reversing the order of steps).

In another embodiment of the present invention, there is provided a process for the preparation of the compound of Formula (5-AA):

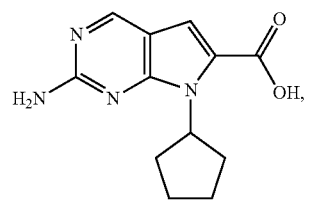

(5-AA)

comprising hydrolyzing the compound of Formula (5-AB):

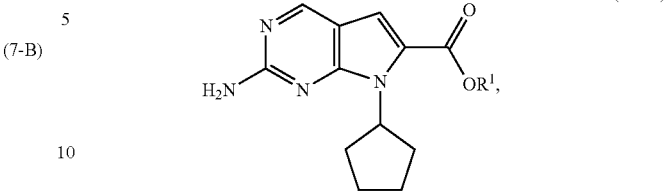

(5-AB)

wherein

R$^1$ is selected from the group consisting of a substituted or unsubstituted aliphatic group having 1 to 10 carbon atoms and a substituted or unsubstituted aryl group having 6 to 14 ring carbon atoms.

Hydrolysis of the compound of Formula (5-AB) is preferably conducted in the presence of a base (B5) and a solvent (S5). Preferably, base (B5) is a metal hydroxide selected from the group consisting of sodium hydroxide, potassium hydroxide and calcium hydroxide. Most preferably, base (B5) is sodium hydroxide. Preferably, solvent (S5) is selected from the group consisting of ethanol, methanol, water and mixtures thereof. Most preferably, solvent (S5) is methanol.

The step of hydrolyzing the compound of Formula (5-AB) may be conducted at any suitable temperature, but is preferably conducted at a temperature between about 0° C. and about 50° C., and more preferably between about 20° C. and about 30° C.

In another embodiment of the present invention, there is provided a process for the preparation of the compound of Formula (4):

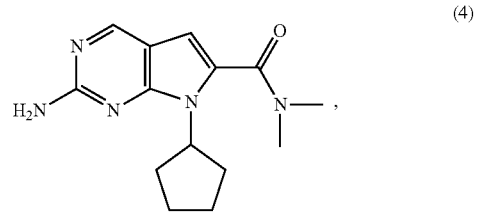 [SMILES: CN(C)C(=O)c1cc2cnc(N)nc2n1C1CCCC1]

(4)

comprising amidating, in the presence of a solvent (S6), a compound of Formula (5-A):

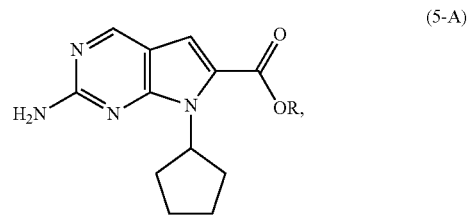

(5-A)

with dimethylamine, or a salt thereof, wherein

R is selected from the group consisting of R$^1$ and H; and

R$^1$ is selected from the group consisting of a substituted or unsubstituted aliphatic group having 1 to 10 carbon atoms and a substituted or unsubstituted aryl group having 6 to 14 ring carbon atoms.

In a preferred embodiment of the amidation, the compound of Formula (5-A) is a compound of Formula (5-AA):

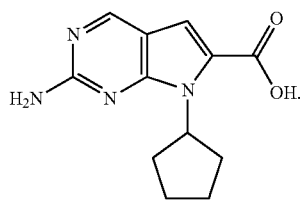

(5-AA)

For the amidation of the compound of Formula (5-AA), a salt form of dimethylamine is preferably used, most preferably, the dihydrochloride salt.

Amidation of the compound of Formula (5-AA) is preferably conducted in the presence of an amide coupling agent. Preferably, the amide coupling agent is selected from the group consisting of carbodiimides, uranium reagents and carbonyldiimidazoles. Preferably, when used, the carbodiimide is used in combination with an additive such as 1-hydroxy-7-azabenzotriazole (HOAt) or 1-hydroxy-1H-benzotriazole (HOBt). Preferably, the carbodiimide is selected from the group consisting of N,N'-dicyclohexylcarbodiimide (DCC), N,N'-diisopropylcarbodiimide (DIC), N-(3-dimethylaminopropyl)-W-ethylcarbodiimide (EDC) and N-(3-dimethylaminopropyl)-W-ethylcarbodiimide hydrochloride (EDC.HCl). Preferably, when used, the uranium reagent is selected from the group consisting of O-(7-azabenzotriazol-1-yl)-1,1,3,3-tetramethyluronium hexafluorophosphate (HATU) and O-(benzotriazol-1-yl)-1,1,3,3-tetramethyluroniumhexafluorophosphate (HBTU). Preferably, when used, the carbonyldiimidazole is selected from the group consisting of 1,1'-carbonyldiimidazole (CDI) and 1,1'-carbonylbis(2-methylimidazole). Most preferably, the amide coupling agent is 1,1'-carbonyldiimidazole.

The amidation of the compound of Formula (5-AA) is conducted in the presence of a solvent (S6). Solvent (S6) is preferably selected from the group consisting of esters, halogenated hydrocarbons and amides. More preferably, solvent (S6) is selected from the group consisting of ethyl acetate, dichloromethane and N,N-dimethylformamide. Most preferably, solvent (S6) is dichloromethane.

Depending on the choice of amide coupling reagent, the step of amidating the compound of Formula (5-AA) may be conducted in the presence of a base (B6). Preferably, when used, base (B6) is a tertiary amine selected from the group consisting of triethylamine and N,N-diisopropylethylamine.

The amidation of the compound of Formula (5-AA) may be conducted at any suitable temperature, and is preferably conducted at a temperature between about 0° C. and about 50° C., and more preferably between about 0° C. and about 15° C.

In an alternative embodiment of the amidation, the compound of Formula (5-A) is a compound of Formula (5-AB):

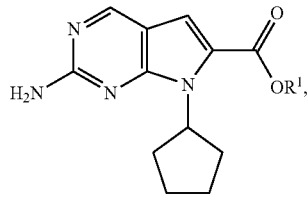

(5-AB)

When amidating the compound of Formula (5-AB), dimethylamine is preferably used as a solution, preferably in a solvent (S6') selected from the group consisting of alcohols and ethers. Preferably, solvent (S6') is selected from the group consisting of methanol, ethanol and tetrahydrofuran.

The amidation of the compound of Formula (5-AB) may be conducted at any suitable temperature, and is preferably conducted at a temperature between about 50° C. and about 90° C., more preferably between about 50° C. and about 70° C. To facilitate completion of the reaction, the step of amidating the compound of Formula (5-AB) with dimethylamine is preferably conducted in a pressure sealed vessel.

In another embodiment of the present invention, there is provided a process for the preparation of Ribociclib (1):

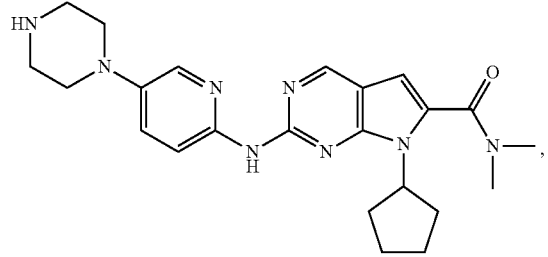

(1)

comprising:
(i) reacting, in the presence of a catalyst, a base (B7) and a solvent (S7), a compound of Formula (4):

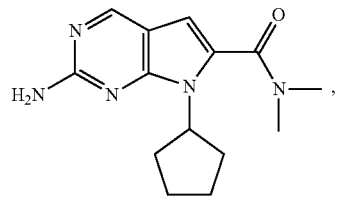

(4)

with a compound of Formula (3):

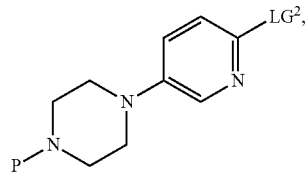

(3)

to provide a compound of Formula (2):

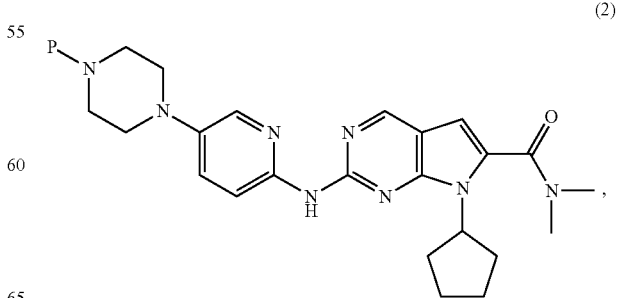

(2)

and
(ii) deprotecting the compound of Formula (2),
wherein
P is a protecting group; and
$LG^2$ is a leaving group.

In the compound of Formula (3), $LG^2$ is a leaving group, preferably selected from the group consisting of halides and sulfonates. Preferred sulfonates are selected from methane sulfonate, toluene sulfonate and trifluoromethane sulfonate. Preferably, $LG^2$ is halide selected from the group consisting of chloride, bromide and iodide, and is most preferably chloride.

In the compound of Formula (3), P is a protecting group, preferably selected from the group consisting of alkyloxycarbonyl groups, benzyloxycarbonyl groups and benzylic groups. Preferred protecting groups are selected from the group consisting of tert-butoxycarbonyl (BOC), benzyloxycarbonyl (CBz), benzyl (Bn) and methoxy substituted benzyl (for example, PMB). Most preferably, the protecting group is tert-butoxycarbonyl.

The reaction of the compound of Formula (4) and the compound of Formula (3) is conducted in the presence of a catalyst, which is preferably comprised of a palladium compound and a tertiary phosphine ligand. The palladium compound is preferably a divalent or zerovalent compound, and is preferably selected from the group consisting of palladium(II) chloride, palladium(II) bromide, palladium(II) acetate, palladium(II) acetylacetonate, bis(benzonitrile)palladium(II) chloride, palladium (II) trifluoroacetate, bis(acetonitrile)palladium(II) chloride, bis(triphenylphosphine) palladium(II) chloride, tris(dibenzylideneacetone)dipalladium (0), bis(dibenzylideneacetone)palladium (0) and tetrakis(triphenylphosphine)palladium (0). Most preferably, the catalyst is bis(dibenzylideneacetone)palladium (0). The tertiary phosphine compound is preferably selected from the group consisting of trialkylphosphines, triarylphosphines, phenoxyphosphines and biarylphosphines, and is most preferably biarylphosphines. Preferably trialkylphosphines are selected from the group consisting of triethylphosphine, tricyclohexylphosphine, triisopropylphosphine, tri-n-butylphosphine, tri-iso-butylphosphine, tri-sec-butylphosphine, and tri-tert-butylphosphine. Preferably, triarylphosphines are selected from the group consisting of triphenylphosphine, tripentafluorophenylphosphine, tri-o-tolylphosphine, tri-m-tolylphosphine, and tri-p-tolylphosphine. Preferably, phenoxyphosphines are selected from the group consisting of tri(2,6-dimethylphenoxy)phosphine, tri(2-tert-butylphenoxy)phosphine, triphenoxy phosphine, tri(4-methylphenoxy)phosphine, and tri(2-methylphenoxy)phosphine. Preferably, biaryl phosphines are selected from the group consisting of 2,2'-bis(diphenylphosphino)-1,1'-binaphthalene (BINAP), 4,5-bis(diphenylphosphino)-9,9-dimethylxanthene (Xantphos) and 2-dicyclohexylphosphino-2',4',6'-triisopropylbiphenyl (Xphos). Most preferably, the biaryl phosphine is 4,5-bis(diphenylphosphino)-9,9-dimethylxanthene (Xantphos). Most preferably, the catalyst is comprised of tris(dibenzylideneacetone)dipalladium (0) and 4,5-bis(diphenylphosphino)-9,9-dimethylxanthene (Xantphos).

The catalyst loading may be from about 1 mol % to about 20 mol % of the palladium compound with respect to the compound of Formula (4). Preferably, the catalyst loading is about 5 mol % palladium with respect to the compound of Formula (4).

The molar ratio of the ligand with respect to the palladium compound may be from 0.2:1 to about 5:1, and preferably about 1.5:1.

The reaction of the compound of Formula (4) and the compound of Formula (3) is conducted in the presence of a solvent (S7). Solvent (S7) is preferably selected from the group consisting of aromatic hydrocarbons and ethers. More preferably, solvent (S7) is selected from the group consisting of toluene, tetrahydrofuran, N,N-dimethylformamide and dioxane. Most preferably, solvent (S7) is dioxane.

The reaction of the compound of Formula (4) and the compound of Formula (3) is conducted in the presence of a base (B7). Base (B7) may be any suitable inorganic or organic base. Suitable bases may be selected from the group consisting of tertiary amines, metal carbonates, metal bicarbonates, metal hydroxides, metal alkoxides and amides. Preferably, base (B7) is a carbonate selected from the group consisting of sodium carbonate, potassium carbonate, cesium carbonate and lithium carbonate. Most preferably, base (B7) is cesium carbonate.

The reaction of the compound of Formula (4) and the compound of Formula (3) may be conducted at any suitable temperature, and is preferably conducted at an elevated temperature at or near the boiling point of the reaction mixture.

In some cases, the compound of Formula (3) is a commercially available compound. Alternatively, compounds of Formula (3) can be prepared by general methods commonly known, including for example, as reported in WO 2012/115118 A1.

In the deprotection of the compound of Formula (2), that is, the removal of the group P, suitable conditions for cleavage of protecting groups from an amine may be employed. For example, suitable methods may be found in Greene, T. W.; Wuts, P. G. M. *Protective Groups in Organic Synthesis*; Fourth edition; Wiley: New York, 2007 and WO 2012/064805 A2.

Preferably, when P is an alkyloxy or carbobenzyloxy carbonyl protecting group such as a BOC or CBz group, the deprotection is conducted by acidolysis using a suitable acid. Suitable acids may be selected from the group consisting of trifluoroacetic acid, methanesulfonic acid, p-toluenesulfonic acid, camphorsulfonic acid, trifluoromethanesulfonic acid, and hydrogen halide. Preferably, the acid is an aqueous solution of hydrogen chloride. The acid may also function as solvent for the deprotection. Alternatively, the deprotection may be conducted in the presence of a solvent selected from the group consisting of aromatic hydrocarbons, chlorinated hydrocarbons and alcohols. Preferably, the solvent is toluene.

When P is a carbobenzyloxy protecting group such as CBz, or a benzylic group, the deprotection may be conducted using hydrogenolysis conditions analogous to the hydrogenating conditions described herein.

The deprotection of a compound of Formula (2) may be conducted at any suitable temperature. Preferably, the temperature is in the range of about 20° C. to about 30° C.

EXAMPLES

The following examples are illustrative of some of the embodiments of the invention described herein. It will be apparent to the person skilled in the art that various alterations to the described processes in respect of the reactants, reagents and conditions may be made when using the processes of the present invention without departing from the scope or intent thereof.

Example 1: Preparation of benzyl 2-(cyclopentylamino)acetate (Compound of Formula (9-A1))

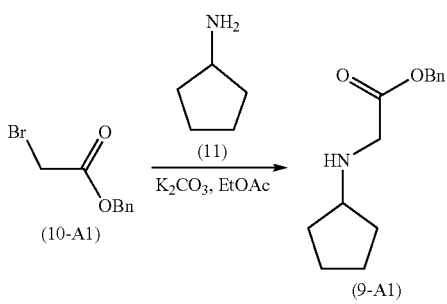 [SMILES: O=C(CBr)OCc1ccccc1 ; NC1CCCC1 ; O=C(CNC1CCCC1)OCc1ccccc1]

To a mixture of the compound of Formula (11) (27.9 g, 1.5 eq) and potassium carbonate (45.2 g, 1.5 eq) in ethyl acetate (250 mL) was added the compound of Formula (10-A1) (50 g, 1.0 eq) dropwise, while maintaining the temperature between about 20° C. to about 30° C. The mixture was stirred at room temperature until the reaction was complete. The resulting suspension was filtered, and the filter cake was washed with ethyl acetate (2×50 mL). The filtrate and washes were combined and concentrated to afford the compound of Formula (9-A1) (51 g, 95% yield, by $^1$H NMR assay) as a light yellow liquid, which was used directly without further purification.

$^1$H-NMR of the compound of Formula (9-A1): (CDCl$_3$, 300 MHz) δ: 7.37~7.31 (5H, m), 5.20 (2H, s), 3.45 (2H, s), 3.09~3.02 (1H, m), 1.84-1.25 (8H, m).

Example 2: Preparation of benzyl 2-((2-amino-6-chloro-5-formylpyrimidin-4-yl)(cyclopentyl)amino) acetate (Compound of Formula (7-A1))

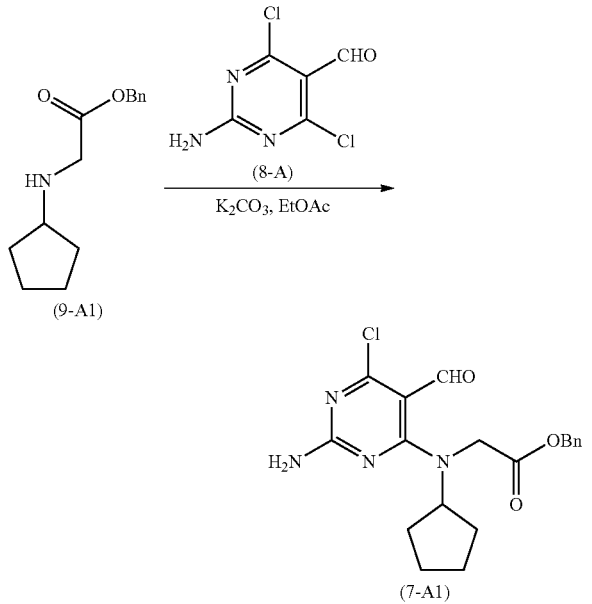

The compound of Formula (9-A1) (10.34 g, 1.1 eq) was added to a mixture of the compound of Formula (8-A) (8.11 g, 1.0 eq) and potassium carbonate (6.4 g, 1.1 eq) in ethyl acetate (48 mL) at room temperature. The mixture was stirred at room temperature until the reaction was complete. The resulting suspension was then collected by filtration. The filter cake was washed with ethyl acetate (16 mL), and water (40 mL) to afford the compound of Formula (7-A1) (18.5 g, 90% yield) as a yellow solid having an HPLC purity of 97.3%). The solid was used directly in the next step without further purification.

$^1$H-NMR of the compound of Formula (7-A1): (DMSO-d$^6$, 300 MHz) δ: 9.93 (1H, s), 7.60~7.41 (5H, m), 5.18 (2H, s), 4.51-4.41 (1H, m), 4.30 (2H, s), 2.07-1.94 (2H, m), 1.70-1.48 (6H, m).

Example 3: Preparation of benzyl 2-amino-4-chloro-7-cyclopentyl-7H-pyrrolo[2,3-d]pyrimidine-6-carboxylate (Compound of Formula (6-A))

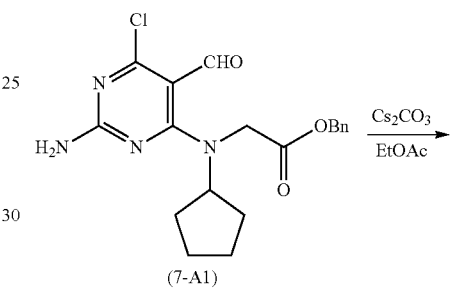

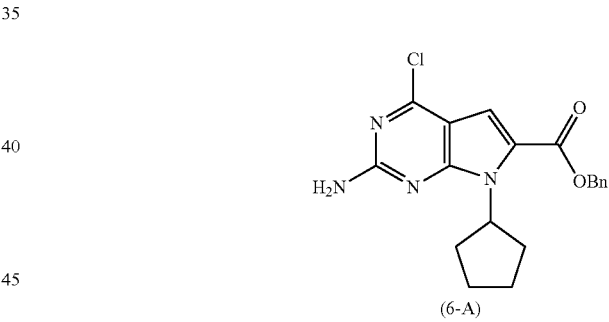

The compound of Formula (7-A1) (14.8 g, 1.0 eq) was charged into the mixture of cesium carbonate (14.8 g, 1.2 eq) in ethyl acetate (150 mL) at room temperature. The suspension was then heated to about 65 to 70° C. until reaction completion, cooled to room temperature, and filtered. The filter cake was washed with ethyl acetate (2×15 mL), and the filtrate was concentrated in vacuo to dryness to afford the compound of Formula (6-A) (11.2 g, 80% yield) as a yellow solid having an HPLC purity of 97.8%, which was used in the next step without further purification.

$^1$H-NMR of the compound of Formula (6-1): (DMSO-d$^6$, 300 MHz) δ: 7.49~7.36 (5H, m), 7.11 (2H, s), 7.09 (1H, s), 5.59~5.50 (1H, m), 5.32 (2H, s), 2.32-2.23 (2H, m), 2.02-1.89 (4H, m), 1.62-1.59 (2H, m).

Example 4: Preparation of 2-amino-7-cyclopentyl-7H-pyrrolo[2,3-d]pyrimidine-6-carboxylic Acid (Compound of Formula (5-AA))

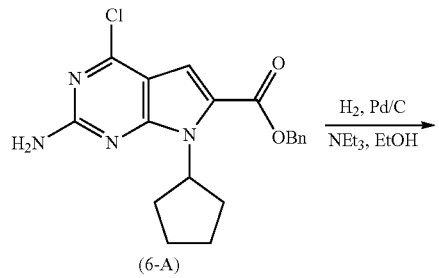

(6-A)

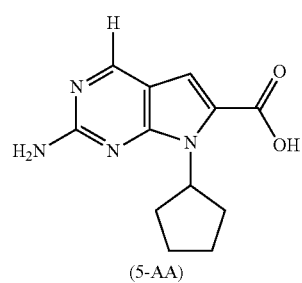

(5-AA)

A mixture of 5 wt % palladium/carbon (0.65 g, 0.25 wt % with respect to (6-1)), the compound of Formula (6-A) (13 g, 1.0 eq) and triethylamine (7.1 g, 2.0 eq) in ethanol (65 mL) was hydrogenated under a pressure (about 15 psi) of hydrogen gas at room temperature until the reaction was complete. The mixture was filtered and the filtrate was concentrated in vacuo to 25-40 mL. Water (65 mL) was added, and the mixture was cooled to 0 to 5° C. before the pH was adjusted to between 6 to 7 with 2N HCl, resulting in a precipitate. The resulting solid was collected by filtration to afford the compound of Formula (5-AA) (7.3 g, 85% yield) as a grey solid having HPLC purity of 98%.

$^1$H-NMR of the compound of Formula (5-AA): (DMSO-$d_6$, 300 MHz) δ: 8.49 (1H, s), 7.08 (1H, d), 5.70-5.58 (1H, m), 2.39-2.35 (2H, m), 2.02-1.85 (4H, m), 1.63-1.56 (2H, m).

Example 5: Preparation of 2-amino-7-cyclopentyl-N,N-dimethyl-7H-pyrrolo[2,3-d]pyrimidine-6-carboxamide (Compound of Formula (4))

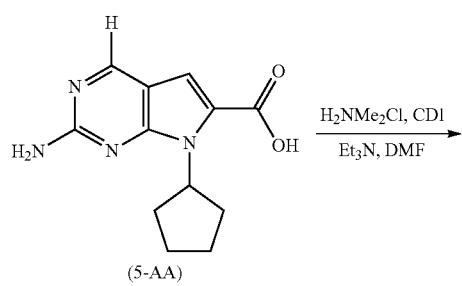

(5-AA)

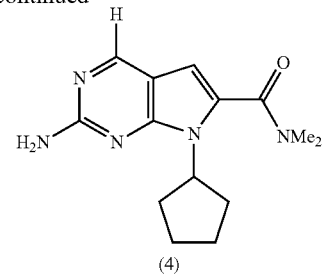

(4)

1,1'-Carbonyldiimidazole (26.3 g, 2.0 eq) and triethylamine (16.4 g, 2.0 eq) were charged into a solution of the compound of Formula (5-AA) (20.0 g, 1.0 eq) in N,N-dimethylformamide (60 mL) at 5 to 10° C. Dimethylamine hydrochloride salt (13.2 g, 2.0 eq) was then added and the reaction mixture was stirred until reaction completion. Water (200 mL) was added dropwise over 1 hour and the mixture was stirred for about 2 hours. The resulting mixture was filtered to afford the compound of Formula (4) (18.2 g, 82% yield) as a grey solid having an HPLC purity of 97%.

$^1$H-NMR of the compound of Formula (4): (DMSO-$d_6$, 300 MHz) δ: 8.51 (1H, s), 6.45 (1H, s), 6.34 (2H, s), 4.93~4.67 (1H, m), 3.03 (6H, s), 2.30-2.23 (2H, m), 1.91-1.89 (4H, m), 1.63-1.41 (2H, m).

Example 6: Preparation of tert-butyl 4-(6-(7-cyclopentyl-6-(dimethylcarbamoyl)-7H-pyrrolo[2,3-d]pyrimidin-2-ylamino)pyridin-3-yl)piperazine-1-carboxylate (Compound of Formula (2-A))

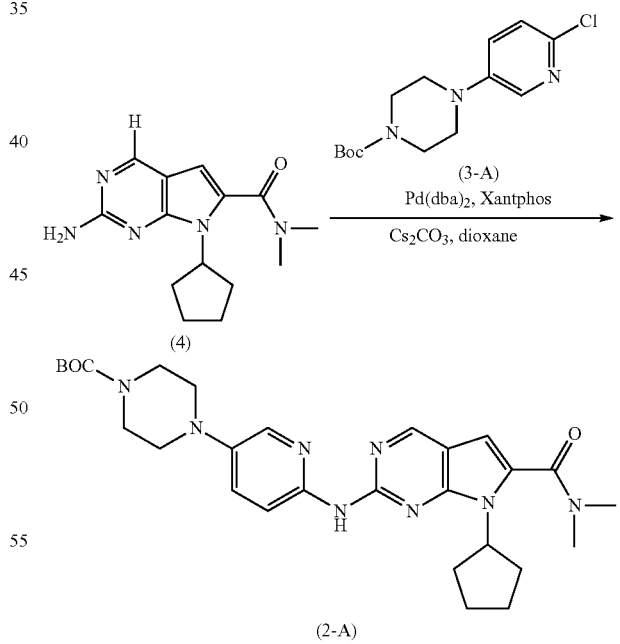

The compound of Formula (4) (6.5 g, 1.0 eq), the compound of Formula (3-A) (7.45 g, 1.05 eq), cesium carbonate (9.32 g, 1.2 eq), bis(dibenzylideneacetone)palladium (0) (1.37 g, 0.1 eq), and Xantphos (2.07 g, 0.15 eq) were combined in 1,4-dioxane (150 mL) at room temperature. The mixture was degassed with nitrogen for about 2 hours, and then maintained at reflux until the reaction was complete. The reaction mixture was cooled to room temperature, filtered, with the filtrate being cooled to about 0 to 5° C., and stirred for about 2 hours. The resulting solid was collected by filtration to afford the compound of Formula (2-A) (10.4 g, 82% yield) as a white solid having HPLC purity of 96%.

$^1$H-NMR of the compound of Formula (2-A): (CDCl$_3$, 300 MHz) δ: 8.78 (1H, s), 8.38 (1H, d), 8.16 (1H, s), 8.05 (1H, d), 7.32 (1H, dd), 6.44 (1H, s), 4.88-4.72 (1H, m), 3.64 (4H, t), 3.16 (6H, s), 3.09 (4H, t), 2.68-2.52 (2H, m), 2.16-1.95 (4H, m), 1.80-1.65 (2H, m), 1.49 (9H, s).

Example 7: Preparation of Ribociclib (1)

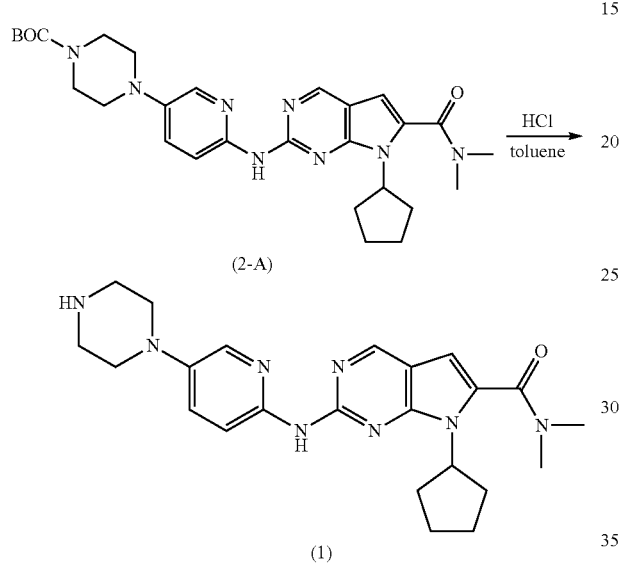

A solution of 1N HCl (6.0 eq) was added to the compound of Formula (2-A) (10.44 g, 1.0 eq) in toluene (105 mL) at 0 to 5° C., and the mixture was stirred at room temperature for 2.5 hours. Following this time, the mixture was extracted with 1N HCl (2×40 mL), and the pH of the aqueous phase was adjusted to 11~12 by charging aqueous NaOH (20 wt %). The resulting precipitate was collected by filtration to afford Ribociclib (1) (7.95 g, 93% yield) as a yellow solid having HPLC purity of 97%.

What is claimed is:

1. A process for the preparation of Ribociclib (1):

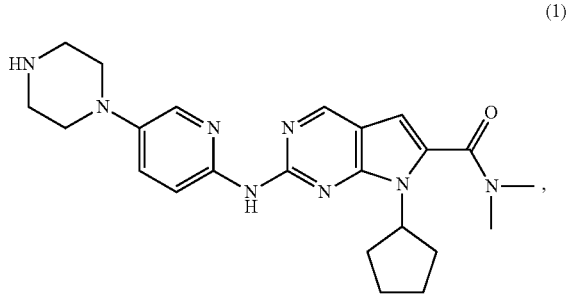 [SMILES: CN(C)C(=O)c1cc2cnc(Nc3ccc(N4CCNCC4)cn3)nc2n1C1CCCC1]

comprising:
(i) reacting, in the presence of a catalyst, a base (B7) and a solvent (S7), a compound of Formula (4):

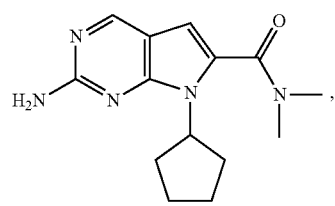

with a compound of Formula (3):

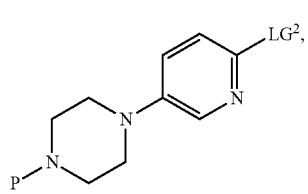

to provide a compound of Formula (2):

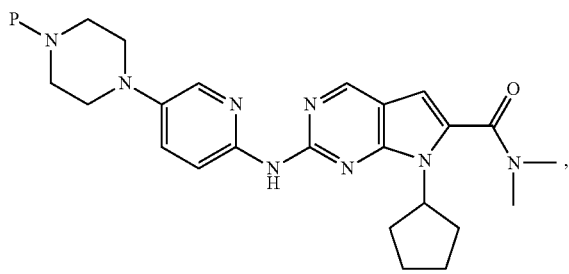

and
(ii) deprotecting the compound of Formula (2), wherein
P is a protecting group; and
LG$^2$ is a leaving group.

2. The process of claim 1, wherein the catalyst is comprised of a palladium compound and a tertiary phosphine ligand.

3. The process of claim 2, wherein the palladium compound is selected from the group consisting of palladium(II) chloride, palladium(II) bromide, palladium(II) acetate, palladium(II) acetylacetonate, bis(benzonitrile)palladium(II) chloride, palladium (II) trifluoroacetate, bis(acetonitrile)palladium(II) chloride, bis(triphenylphosphine)palladium(II) chloride, tris(dibenzylideneacetone)dipalladium (0), bis(dibenzylideneacetone)palladium (0) and tetrakis(triphenylphosphine)palladium (0).

4. The process of claim 3, wherein the tertiary phosphine ligand is selected from the group consisting of 2,2'-bis(diphenylphosphino)-1,1'-binaphthalene, 4,5-bis(diphenylphosphino)-9,9-dimethylxanthene and 2-dicyclohexylphosphino-2',4',6'-triisopropylbiphenyl.

5. The process of claim 1, wherein the catalyst is comprised of bis(dibenzylideneacetone)palladium (0) and 4,5-bis(diphenylphosphino)-9,9-dimethylxanthene.

6. The process of claim 4, wherein LG$^2$ is chloride.

7. The process of claim 6, wherein P is a tert-butoxycarbonyl (BOC) group.

8. The process of claim 1, wherein the compound of Formula (4) is prepared by amidating, in the presence of a solvent (S6), a compound of Formula (5-A):

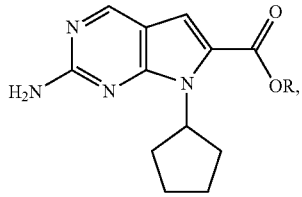
(5-A)

with dimethylamine, or a salt thereof,
wherein
R is selected from the group consisting of $R^1$ and H; and
$R^1$ is selected from the group consisting of a substituted or unsubstituted aliphatic group having 1 to 10 carbon atoms and a substituted or unsubstituted aryl group having 6 to 14 ring carbon atoms.

9. The process of claim 8, wherein the compound of Formula (5-A) is a compound of Formula (5-AA):

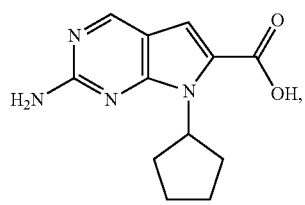
(5-AA)

and the step of amidating is conducted in the presence of an amide coupling agent selected from the group consisting of carbodiimides, uranium reagents and carbonyldiimidazoles.

10. The process of claim 9, wherein the amide coupling agent is carbonyldiimidazole.

11. The process of claim 9, wherein the compound of Formula (5-AA) is prepared by a process comprising hydrogenating, in the presence of a solvent (S4) and a base (B4), a compound of Formula (6):

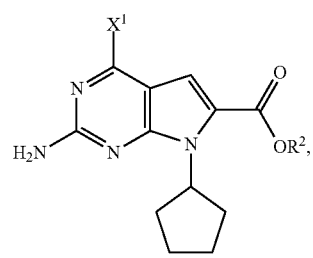
(6)

wherein
$X^1$ is halide or H;
$R^2$ is $CR^aR^bR^c$;
$R^a$, $R^b$ and $R^c$ are three independent groups selected from the group consisting of H, a substituted aryl group having 6 to 14 ring carbon atoms and an unsubstituted aryl group having 6 to 14 ring carbon atoms; and
at least one of the groups $R^a$, $R^b$ and $R^c$ is a substituted aryl group having 6 to 14 ring carbon atoms or an unsubstituted aryl group having 6 to 14 ring carbon atoms.

12. The process of claim 11, wherein $R^2$ is benzyl or substituted benzyl.

13. The process of claim 12, wherein the hydrogenating step comprises treating the compound of Formula (6) with hydrogen gas in the presence of a palladium on carbon catalyst.

14. The process of claim 11, wherein the compound of Formula (6) is prepared by a process comprising:

(i) reacting, in the presence of a base (B1) and a solvent (S1), a compound of Formula (11):

(11)

with a compound of Formula (10-A):

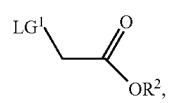
(10-A)

to provide a compound of Formula (9-A):

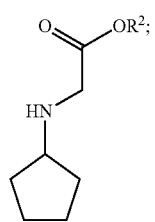
(9-A)

(ii) reacting, in the presence of a base (B2) and a solvent (S2), the compound of Formula (9-A) with a compound of Formula (8):

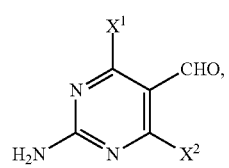
(8)

to provide a compound of Formula (7-A):

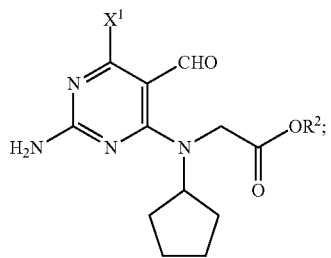
(7-A)

and (iii) cyclizing, in the presence of a base (B3) and a solvent (S3), the compound of Formula (7-A) to provide the compound of Formula (6), wherein
$R^2$ is $CR^aR^bR^c$;
$R^a$, $R^b$ and $R^c$ are three independent groups selected from the group consisting of H, a substituted aryl group having 6 to 14 ring carbon atoms and an unsubstituted aryl group having 6 to 14 ring carbon atoms;
at least one of the groups $R^a$, $R^b$ and $R^c$ is a substituted aryl group having 6 to 14 ring carbon atoms or an unsubstituted aryl group having 6 to 14 ring carbon atoms;
$X^1$ is halide or H;
$X^2$ is halide; and
$LG^1$ is a leaving group.

15. The process of claim 14, wherein each of $X^1$, $X^2$ and $LG^1$ are independently halide.

16. The process of claim 15, wherein $R^2$ is benzyl or substituted benzyl.

* * * * *